(12) United States Patent
Joy et al.

(10) Patent No.: US 10,118,887 B2
(45) Date of Patent: Nov. 6, 2018

(54) ALKYL ALPHA-HYDROXYMETHYL ACRYLATES AS REACTIVE SURFACTANTS IN EMULSION POLYMERIZATION

(71) Applicants: Abraham Joy, Copley, OH (US); Chao Peng, Cuyahoga Falls, OH (US)

(72) Inventors: Abraham Joy, Copley, OH (US); Chao Peng, Cuyahoga Falls, OH (US)

(73) Assignee: The University of Akron, Akron, OH (US)

( * ) Notice: Subject to any disclaimer, the term of this patent is extended or adjusted under 35 U.S.C. 154(b) by 182 days.

(21) Appl. No.: 14/832,459

(22) Filed: Aug. 21, 2015

(65) Prior Publication Data

US 2016/0052858 A1 Feb. 25, 2016

Related U.S. Application Data

(60) Provisional application No. 62/040,040, filed on Aug. 21, 2014.

(51) Int. Cl.
*C07C 69/732* (2006.01)
*C08F 220/20* (2006.01)
*C08F 220/18* (2006.01)
*C08L 33/06* (2006.01)

(52) U.S. Cl.
CPC .......... *C07C 69/732* (2013.01); *C08F 220/20* (2013.01); *C08F 220/18* (2013.01); *C08L 33/06* (2013.01)

(58) Field of Classification Search
CPC .... C07C 69/732; C07C 2101/14; C08F 20/28
USPC .......................................... 524/833
See application file for complete search history.

(56) References Cited

U.S. PATENT DOCUMENTS

| | | | | |
|---|---|---|---|---|
| 3,288,883 | A * | 11/1966 | Temin ................ | C08F 220/28 525/118 |
| 6,320,000 | B1 * | 11/2001 | Hurry ................ | B01J 19/002 526/67 |
| 6,353,087 | B1 * | 3/2002 | Chang-Mateu ......... | C08F 6/003 528/481 |
| 7,041,846 | B2 * | 5/2006 | Watanabe ............ | C07C 69/732 560/128 |
| 2003/0225168 | A1 * | 12/2003 | Deroo ............... | C08F 2/32 516/77 |

FOREIGN PATENT DOCUMENTS

JP 06135896 A * 5/1994 ........... C07C 69/732

OTHER PUBLICATIONS

Machine translation of JP 06135896 A, Kita et al. published May 1994 (Year: 1994).*

* cited by examiner

*Primary Examiner* — Jane L Stanley
(74) *Attorney, Agent, or Firm* — Renner Kenner Greive Bobak Taylor & Weber (57) ABSTRACT

Polymers including α-hydroxymethylacrylate units and methods of preparing polymers from α-hydroxymethylacrylates are provided. Advantageously, α-hydroxymethylacrylates may be used in an emulsion polymerization and function as a polymerizable surfactant. The ability of the α-hydroxymethylacrylates to be used as a polymerizable surfactant allows for emulsion polymerization systems to be prepared without other surfactants.

16 Claims, 4 Drawing Sheets

ALKYL ALPHA-HYDROXYMETHYL ACRYLATES AS REACTIVE SURFACTANTS IN EMULSION POLYMERIZATION

CROSS-REFERENCE TO RELATED APPLICATIONS

This application claims priority from U.S. provisional patent application Ser. No. 62/040,040 filed on Aug. 21, 2014, which is incorporated herein by reference in its entirety.

FIELD OF THE INVENTION

One or more embodiments provides an emulsion polymerization of alkyl alpha-hydroxymethyl acrylate monomers.

BACKGROUND OF THE INVENTION

Emulsion polymerization is a very useful technique for polymer synthesis, and is widely used in academic and industrial fields for the synthesis of several commodity and engineering polymers, such as poly(methyl methacrylate), poly(vinyl acetate), vinyl acetate copolymers and butadiene-styrene copolymers. The major advantages of emulsion polymerization include fast polymerization rates, high conversion, low viscosity and efficient heat dissipation. Moreover, using water as the reaction medium is cheap and environmentally friendly compared to the use of volatile organic solvents. The product of an emulsion polymerization, which is referred to as latex, can be readily used in a variety of applications such as paints, adhesives and textile coatings. A key component in an emulsion polymerization system is the surfactant (in the range of a few tenths of a percent to 5%), which stabilizes the emulsion. However, the use of surfactants could have negative effects on the properties of the product due to surfactant migration through the polymeric material which in turn affects the water uptake of the product and causes plasticization.

In light of this, there have been reports on the synthesis of polymers via surfactant-free emulsion polymerization (SFEP), for example by the use of ionic initiators, surfactant-free emulsion RAFT (reversible addition-fragmentation chain transfer) polymerization, and polymerizable surfactants.

Presently, there exists a need for new polymerizable surfactants that may be used in a self-emulsion polymerization to mitigate the adverse effect of surfactant migration. Particularly useful polymerizable surfactants will have a structure that is homologous with conventional monomers.

SUMMARY OF THE INVENTION

In a first embodiment, an α-hydroxymethylacrylate is provided defined by the formula where $R^2$ is a hydrocarbon group with at least 3 carbon atoms.

In a second embodiment an α-hydroxymethylacrylate is provided as in the first embodiment, wherein $R^2$ is a linear or branched alkyl group.

In a third embodiment an α-hydroxymethylacrylate is provided as in either the first or second embodiment, wherein $R^2$ has from about 4 to about 18 carbon atoms.

In a fourth embodiment an α-hydroxymethylacrylate is provided as in any of the first through third embodiments, wherein $R^2$ is selected from the group consisting of n-propyl, n-butyl, t-butyl, n-pentyl, n-hexyl, 2-ethylhexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, and benzyl.

In a fifth embodiment a method of preparing a polymer is provided comprising an emulsion polymerization of an α-hydroxymethylacrylate.

In a sixth embodiment a method of preparing a polymer is provided as in the fifth embodiment, wherein the emulsion polymerization is a surfactant-free emulsion polymerization.

In a seventh embodiment a method of preparing a polymer is provided as in either the fifth or sixth embodiments, wherein the polymerization is initiated with water-soluble free radical initiator.

In an eighth embodiment a method of preparing a polymer is provided as in any of the fifth through seventh embodiments, wherein the polymerization is mediated with a Reversible Addition-Fragmentation chain Transfer (RAFT) agent.

In a ninth embodiment a method of preparing a polymer is provided as in any of the fifth through eighth embodiments, wherein the α-hydroxymethylacrylate is defined by the formula:

where $R^2$ is a hydrocarbon group with at least 3 carbon atoms.

In a tenth embodiment a method of preparing a polymer is provided as in any of the fifth through ninth embodiments, wherein the polymerization further includes a monomer selected from the group consisting of acrylonitrile, alkyl acrylates, alkyl methacrylates, acrylic acid, methacrylic acid, styrene, and combinations thereof.

In an eleventh embodiment a method of preparing a polymer is provided as in any of the fifth through tenth embodiments, wherein the emulsion polymerization produces a polymer with an α-hydroxymethylacrylate unit that includes a hydroxyl group defined by the following formula where $R^2$ is a hydrocarbon group with at least 3 carbon atoms.

In a twelfth embodiment a method of preparing a polymer is provided as in any of the fifth through eleventh embodiments, wherein the hydroxyl group is reacted with compound selected from esters, carboxylic acid anhydrides, halogen phosphonates, lactones, cyclic carbonates, and lactides.

In a thirteenth embodiment a latex polymer is provided comprising a polymer with units derived from the polymerization of an α-hydroxymethylacrylate.

In a fourteenth embodiment a latex polymer is provided as in the thirteenth embodiment, wherein at least 5% of the polymer units are derived from the polymerization of α-hydroxymethylacrylate.

In a fifteenth embodiment a latex polymer is provided as in as in either the thirteenth or fourteenth embodiments, wherein the polymer further includes units derived from polymerization selected from the group consisting of acrylonitrile, alkyl acrylates, alkyl methacrylates, acrylic acid, methacrylic acid, styrene, and combinations thereof.

In a sixteenth embodiment a latex polymer is provided as in any of the thirteenth through fifteenth embodiments, wherein the polymer is defined by the formula where each $R^2$ is individually a hydrocarbon group and n is about 100 to about 2000 units.

In a seventeenth embodiment a latex polymer is provided as in any of the thirteenth through sixteenth embodiments, wherein the polymer is defined by the formula where each $R^2$ is individually a hydrocarbon group, each $R^3$ is individually the side chain of a acrylonitrile, alkyl acrylates, alkyl methacrylates, acrylic acid, methacrylic acid, styrene, each $R^4$ is individually a hydrogen atom or a hydrocarbon group, and n is about 100 to about 5000 units, and o is about 100 to about 10000 units.

In an eighteenth embodiment a latex polymer is provided as in any of the thirteenth through seventeenth embodiments, wherein the polymer is defined by the formula where each $R^2$ is individually a hydrocarbon group, n is about 50 to about 1000 units, and Z is a segment of a RAFT agent.

In a nineteenth embodiment a latex polymer is provided as in any of the thirteenth through eighteenth embodiments, wherein the polymer is defined by the formula where each $R^2$ is individually a hydrocarbon group, each $R^3$ is individually the side chain of a acrylonitrile, alkyl acrylates, alkyl methacrylates, acrylic acid, methacrylic acid, or styrene monomer, each $R^4$ is individually a hydrogen atom or a hydrocarbon group, n is about 50 to about 1000 units, o is about 50 to about 1000 units, and Z a segment of a RAFT agent.

DETAILED DESCRIPTION OF ILLUSTRATIVE EMBODIMENTS

According to one or more embodiments, an emulsion polymerization of an α-hydroxymethylacrylate is provided. It has been found α-hydroxymethylacrylates may be used as polymerizable surfactants in emulsion polymerizations. Advantageously, α-hydroxymethylacrylates may be polymerized, optionally with a copolymer, in an emulsion polymerization without the need for conventional emulsion polymerization surfactants. This type of polymerization may be referred to as a surfactant-free emulsion polymerization (SFEP). A latex prepared from the emulsion polymerization of an α-hydroxymethylacrylate may be used in adhesives and coatings.

In one or more embodiments, the α-hydroxymethylacrylates may be defined by the formula:

where $R^2$ is a hydrocarbon group.

Suitable hydrocarbon groups for use in an α-hydroxymethylacrylate or a polymer prepared from an α-hydroxymethylacrylate may be linear, cyclic, or branched alkyl groups. In certain embodiments, the hydrocarbon group may be aromatic or include an aromatic moiety.

In one or more embodiments, the hydrocarbon group, $R^2$, may be characterized by the number of carbon atoms in the group. In one or more embodiments, a hydrocarbon group suitable for use as an $R^2$ has a number of carbon atoms sufficient to allow the α-hydroxymethylacrylate to be used as a polymerizable surfactant. In these or other embodiments, $R^2$ has at least 3 carbon atoms, and in other embodiments $R^2$ has at least 4 carbon atoms. Those skilled in the art will appreciate that the maximum number of carbon atoms in hydrocarbon group, $R^2$, may be selected to achieve certain properties such as critical micelle concentration or the glass transition temperature of the polymer. In one or other embodiments, $R^2$ has at most 18 carbon atoms, in other embodiments at most 16 carbon atoms, and in other embodiments at most 12 carbon atoms. In one or more embodiments, the $R^2$ has from about 3 to about 18 carbon atoms, in other embodiments from about 4 to about 16 carbon atoms, and in other embodiments from about 5 to about 12 carbon atoms.

Suitable hydrocarbon groups for use as an $R^2$ in an α-hydroxymethylacrylate include, but are not limited to n-propyl, n-butyl, t-butyl, n-pentyl, n-hexyl, 2-ethylhexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, and benzyl.

Specific examples of α-hydroxymethylacrylates include, but are not limited to, ethyl α-hydroxymethyl acrylate, n-butyl α-hydroxymethyl acrylate, n-hexyl α-hydroxymethyl acrylate, and 2-ethylhexyl α-hydroxymethyl acrylate.

In one or more embodiments, the α-hydroxymethylacrylate may be prepared by a Baylis-Hillman reaction. The Baylis-Hillman reaction is a carbon-carbon bond forming reaction between a carbon electrophile and an activated alkene in presence of a tertiary amine. The Baylis-Hillman reaction may be performed as a one-pot process. Suitable tertiary amines for use in the Baylis-Hillman reaction include, but are not limited to, DABCO (1,4-diazabicyclo [2.2.2]octane), Quinuclidine, 3-hydroxyquinuclidine, 3-quinuclidone, indolizine, and triethylamine. Suitable solvent conditions or systems for performing the Baylis-Hillman reaction include but are not limited to neat, dioxane/water, tetrahydrofuran (THF)/water.

In one or more embodiments, where the α-hydroxymethylacrylates is formed through a Baylis-Hillman reaction, the α-hydroxymethylacrylates may be a Baylis-Hillman adduct of the following reactants:

where $R^2$ is a hydrocarbon group.

As indicated above, α-hydroxymethylacrylates are particularly useful as monomers or polymerizable surfactants in emulsion polymerizations. The α-hydroxymethylacrylates, and optionally a co-monomer, may be polymerized through emulsion polymerization to form a latex. In these or other embodiments, an emulsion polymerization system may be prepared by combining α-hydroxymethylacrylates, and optionally a co-monomer, with an initiator in water. The initiator may be introduced to the water along with the α-hydroxymethylacrylate or after the α-hydroxymethylacrylate is introduced. In one or more embodiments, the emulsion polymerization system may also include a reversible addition-fragmentation chain-transfer (RAFT) agent. The emulsion polymerization system should be mixed during the polymerization. In one or more embodiments, the formation of a micelle in the emulsion polymerization system is assisted through sonication.

The temperature of the polymerization may be controlled during the polymerization. Suitable methods of controlling the temperature include oil baths. In one or more embodiments, the temperature may be from about 45° C. to about 90° C., in other embodiments from about 55° C. to about 80° C., and in other embodiments from about 65° C. to about 75° C.

In one or more embodiments, the emulsion polymerization may be allowed to proceed until monomer conversion is complete or sufficiently complete. Sufficiently complete monomer conversion refers to a polymerization where almost all of the monomer has been polymerized. In other embodiments, polymerization may be terminated before monomer conversion is complete. In one or more embodiments, the emulsion polymerization may be allowed to proceed for at least 45 minutes, in other embodiments for at least 60 minutes, and in other embodiments for at least 80 minutes. In one or more embodiments, the emulsion polymerization may be allowed to proceed for at most 180 minutes, in other embodiments for at most 120 minutes, and in other embodiments for at most 120 minutes. In one or more embodiments, the emulsion polymerization may be allowed to proceed from about 45 minutes to about 180 minutes, in other embodiments from about 60 minutes to about 120 minutes, and in other embodiments from about 80 minutes to about 120 minutes.

In certain embodiment, the emulsion polymerization system may include adjuvants such as salts. For example, NaHCO3 may be used to increase the solubility of certain initiators.

While α-hydroxymethylacrylates may function as a polymerizable surfactant, in certain embodiments, a conventional emulsion polymerization surfactants may be included in the emulsion polymerization system. conventional emulsion polymerization surfactants refer to surfactants that assist in the formation of an emulsion, but are not polymerizable. Conventional emulsion polymerization surfactants may simply be referred to as surfactants. Suitable surfactants include anionic, nonionic, and cationic surfactants. Specific examples of surfactants include, but are not limited to fatty acids, sodium dodecyl sulfate, and octaethylene glycol monododecyl ethers.

In one or more embodiments, where a conventional emulsion polymerization surfactant is employed, the amount of the conventional emulsion polymerization surfactants may be characterized by the molar percent of the total monomer content (i.e. the moles of surfactant divided by the moles of monomer multiplied by 100). In one or more embodiments, the amount of surfactant may be from about 0.5% to about 5%, in other embodiments from about 1% to about 4%, and in other embodiments from about 2% to about 3%. In other embodiments, the polymerization may take place in the absence of a conventional emulsion polymerization surfactant.

In one or more embodiments, the initiator is a water-soluble free radical initiator. Suitable water-soluble free radical initiators include 4,4'-azobis(4-cyanovaleric acid), potassium persulfate, sodium persulfate, 2,2'-Azobis[2-(2-imidazolin-2-yl)propane], and 2,2'-Azobis(2-methylpropionamidine)dihydrochloride.

The amount of initiator in may be characterized by molar percent of the total monomer content. In one or more embodiments, the amount of initiator may be from about 0.1% to about 5%, in other embodiments from about 1% to about 4%, and in other embodiments from about 2% to about 3%.

As noted above, a RAFT agent may be included in the emulsion polymerization system. In these embodiments, the polymerization of the α-hydroxymethylacrylate, and any optional co-monomer, may be mediated through a reversible addition-fragmentation chain-transfer polymerization. In one or more embodiments, the reversible addition-fragmentation chain-transfer polymerization is mediated by a RAFT agent with a thiocarbonylthio group. In one or more embodiments, the RAFT agent with a thiocarbonylthio group defined by the formula:

where R is the free radical leaving group that is capable of reinitiating polymerization and Z is a group that controls C=S bond reactivity. The Z group that controls C=S bond reactivity influences the rate of radical addition and fragmentation. In these or other embodiments, the thiocarbonylthio group of the RAFT agent is a dithioester, dithiocarbamate, trithiocarbonate, or a xanthate group.

Suitable Raft polymerization agents are disclosed in WO 98/01478 and WO 99/31144, which are both incorporated by reference.

In one or more embodiments, the reversible addition-fragmentation chain-transfer polymerization is mediated by a RAFT agent selected from the group consisting of 2-(dodecylthiocarbonothioylthio)-2-methylpropionic acid, 2-(butylthiocarbonothioylthio)-2-methylpropionic acid 4-cyano-4-(phenylcarbonothioylthio) pentanoic acid.

In one or more embodiments, the amount of α-hydroxymethylacrylate in the emulsion polymerization system should be greater than the CMC of the α-hydroxymethylacrylate. In these or other embodiments, the amount of the α-hydroxymethylacrylate in emulsion polymerization system may have a molar percent greater 1% in other embodiments greater than 3%, and in other embodiments greater than 5%

As noted above, the α-hydroxymethylacrylates may be polymerized along with co-monomer. In these or other embodiments, the percent of α-hydroxymethylacrylates may be characterized by the molar percent of the total monomer content. The total monomer content may be described as the moles of α-hydroxymethylacrylate content and the moles of any co-monomer. In one or more embodiments, the α-hydroxymethylacrylate is at least 5, in other embodiments at least 10, and in other embodiments at least 15 molar percent of the total monomer content. In these or other embodiments, the α-hydroxymethylacrylate is at most 80, in other embodiments at most 90, and in other embodiments at most 99 molar percent of the total monomer content. In these or other embodiments, the α-hydroxymethylacrylate is from about 5 to about 99, in other embodiments from about 10 to about 90, and in other embodiments from about 15 to about 80 weight percent of the total monomer content.

Suitable co-monomers include those that contain a vinyl group. Examples of include co-monomers, include but are not limited to, acrylonitrile, alkyl acrylates, alkyl methacrylates, acrylic acid, methacrylic acid, styrene, and combinations thereof.

In one or more embodiments, the co-monomer may be a functionalized acrylic monomer. A functionalized acrylic monomer refers to an acrylate or methacrylate monomers with functional groups other than an alkyl group. Examples of functionalized acrylic monomers may be found in WO 2014/152850, which is incorporated herein by reference.

Specific examples functionalized acrylic monomers may be defined by the following formula:

where $R^6$ is a hydrogen atom or a methyl group and the $R^5$ group may be selected from —$(CH_2)_x$—NHBoc, —$(CH_2)_x$—COOtBu, —$(CH_2)_x$—OTBDMS, and —$(CH2)x$-$N3$, —$(CH2)x$-C≡CH, where X may be 1 to 6 units.

Specific examples of alkyl acrylates include, but are not limited to, methyl acrylate, ethyl acrylate, propyl acrylate, n-butyl acrylate, isobutyl acrylate.

Specific examples of alkyl methacrylates include, but are not limited to, methyl methacrylate, ethyl methacrylate, propyl methacrylate, n-butyl methacrylate, isobutyl methacrylate.

The result of the emulsion polymerization is a polymer with units derived from the polymerization of α-hydroxymethylacrylate. In one or more embodiments the polymer may also include units derived from co-monomer. For the purpose of this disclosure derived units refers to the mer units that result from the monomers that have been reacted to form the polymer. In one or more embodiments, the polymer with units derived from the polymerization of α-hydroxymethylacrylate is part of a latex. In these or other embodiments, the polymer with units derived from the polymerization of α-hydroxymethylacrylate may form or be included in a latex particle.

In one or more embodiments, the polymer with units derived from the polymerization of α-hydroxymethylacrylate may be defined by the following formula:

where each $R^2$ is individually a hydrocarbon group and n is about 100 to about 2000 units.

In certain embodiments, where the α-hydroxymethylacrylate is polymerized with a co-monomer, the polymer with units derived from the polymerization of α-hydroxymethylacrylate may be defined by the following formula:

where each $R^2$ is individually a hydrocarbon group, each $R^3$ is individually the side chain of a acrylonitrile, alkyl acrylates, alkyl methacrylates, acrylic acid, methacrylic acid, and styrene, each $R^4$ is individually a hydrogen atom or a hydrocarbon group, and n is about 100 to about 5000 units, and o is about 100 to about 10000 units.

In one or more embodiments, where the emulsion polymerization is mediated with a RAFT agent, the polymer with units derived from the polymerization of α-hydroxymethylacrylate may be defined by the following formula:

where each $R^2$ is individually a hydrocarbon group, n is about 50 to about 1000 units, and Z is a segment of a RAFT agent. A segment of a RAFT agent may be a group adjacent to the thiocarbonylthio group on a RAFT agent. For example, the group that controls C=S bond reactivity.

In certain embodiments, where the emulsion polymerization is mediated with a RAFT agent and the α-hydroxymethylacrylate is polymerized with a co-monomer, the polymer with units derived the polymerization an α-hydroxymethylacrylate may be defined by the following formula:

where each $R^2$ is individually a hydrocarbon group, each $R^3$ is individually the side chain of a acrylonitrile, alkyl acrylates, alkyl methacrylates, acrylic acid, methacrylic acid, or styrene monomer, each $R^4$ is individually a hydrogen atom or a hydrocarbon group, n is about 50 to about 1000 units, o is about 50 to about 1000 units, and Z a segment of a RAFT agent. A segment of a raft agent may be a group adjacent to the thiocarbonylthio group on a RAFT agent. For example, the group that controls C=S bond reactivity.

Advantageously, a polymer with units derived from the polymerization of α-hydroxymethylacrylate includes a hydroxyl group that may be included in further reactions after polymerization. Specific examples of compounds capable of reacting with a hydroxyl group on a unit derived from α-hydroxymethylacrylate include esters, carboxylic acid anhydrides, halogen phosphonates, lactones, cyclic carbonates, and lactides. In certain embodiments, when the hydroxyl group on a unit derived from α-hydroxymethylacrylate is reacted with a lactone, a polyester polymer or oligomer may be pendently attached to the unit derived from α-hydroxymethylacrylate.

Specific compounds that may be reacted with the hydroxyl group include, but are not limited to,

Exemplary reactions schemes of reaction at the hydroxyl group on a unit derived from α-hydroxymethylacrylate include:

While particular embodiments of the invention have been disclosed in detail herein, it should be appreciated that the invention is not limited thereto or thereby inasmuch as variations on the invention herein will be readily appreciated by those of ordinary skill in the art. The scope of the invention shall be appreciated from the claims that follow.

EXAMPLES

The self-emulsion polymerization of three types of alkyl α-hydroxymethyl acrylates with different pendant groups (ethyl [1], n-butyl [2] and n-hexyl [3]) was investigated. The monomers are products of the Baylis-Hillman reaction and were synthesized by a one-step reaction of formaldehyde with the corresponding alkyl acrylate in the presence of DABCO/Et3N in THF/H2O The critical micelle concentrations of the three monomers were determined using two methods: surface tension and dynamic light scattering (DLS) (Table 1). The surface tension method provides a clearer indication of the formation of micelles. For the polymerizations described below, the monomer concentration was higher than the corresponding CMC measured by either method.

TABLE 1

Conventional radical polymerization of alkyl α-hydroxymethyl acrylate via SEP

| Polymer[a] | Monomer | CMC of the monomer (mM) Surface tension | DLS | $M_n^{SEC}$ (kDa) | PDI $(M_w/M_n)$ | Conversion (%) [b] | $D_z$ (μm)[e] |
|---|---|---|---|---|---|---|---|
| P1 | 1 | 5.3 | 16.3 | 88.6[c] | 1.64[c] | 63 | 0.83 |
| P2 | 2 | 1.6 | 13.1 | 115.4[d] | 1.45[d] | 96 | 1.30 |
| P3 | 3 | 0.4 | 2.2 | 143.6[c] | 1.53[c] | 98 | 0.85 |

P1: poly(ethyl a-hydroxymethyl acrylate)
P2: poly(n-butyl a-hydroxymethyl acrylate)
P3: poly(n-hexyl a-hydroxymethyl acrylate)
[a]All the experiments were carried out at 70° C. for 90 minutes.
[b]Monomer conversion determined by $^1$H NMR.
[c]Determined by SEC using DMF as the eluent.
[d]Determined by SEC using THF as the eluent.
[e]The average diameter $D_z$ was determined by dynamic light scattering (DLS).

The conventional radical polymerization of the three monomers was first performed via self-emulsion polymerization (SEP). The polymerization was initiated by a water-soluble initiator 4,4'-azobis(4-cyanovaleric acid) (ABCVA) which was neutralized by NaHCO3 prior to polymerization. The polymerization was carried out at 70° C. in water for 90 minutes. The three polymers were obtained with number average molecular weights around 100 kDa and a PDI around 1.5 (Table 1). The polymerization of 2 and 3 reached almost quantitative conversion after 90 minutes, as determined by 1H NMR integration of the backbone methylene protons relative to the vinyl protons of the monomer. The polymerization of 1 is not as efficient as that of 2 and 3. Monomer 1 has higher water solubility due to its short ethyl side chain. Thus solution polymerization in water would compete with polymerization within the emulsion particles, resulting in a slower reaction rate.

Figure 1:
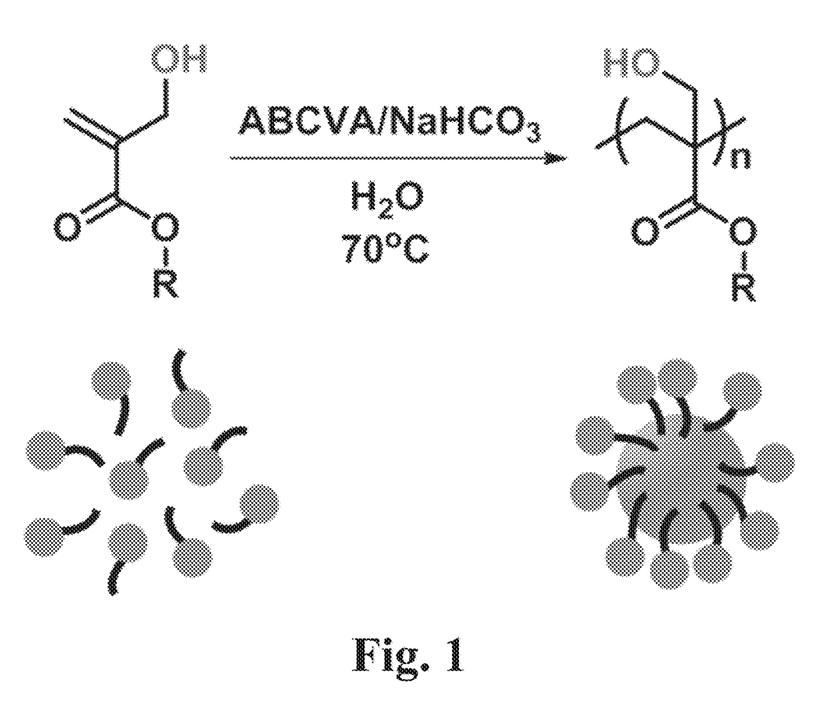
FIG. 1 provides a scheme for the self-emulsion polymerization of one or more embodiments.
Figure 2A:
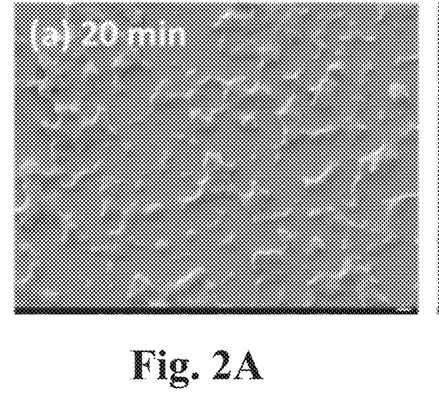
FIG. 2A provides an SEM image showing the formation of latex particles prepared from the polymerization of n-butyl α-hydroxymethyl acrylate at 20 minutes. The scale bar is 1 μm. The particle size determined by DLS is 0.60 μm.
Figure 2B:
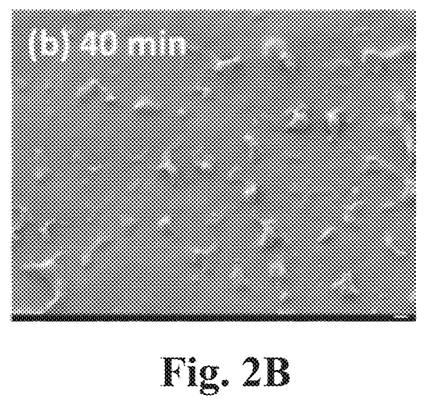
FIG. 2B provides an SEM image showing the formation of latex particles prepared from the polymerization of n-butyl α-hydroxymethyl acrylate at 40 minutes. The scale bar is 1 μm. The particle size determined by DLS is 1.06 μm.
Figure 2C:
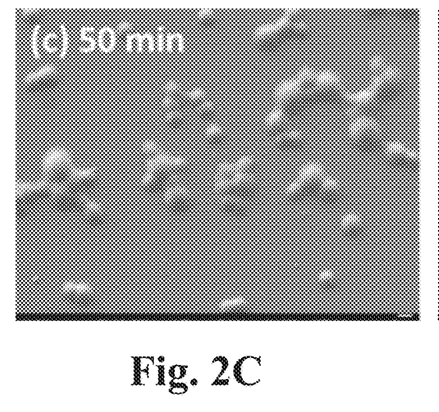
FIG. 2C provides an SEM image showing the formation of latex particles prepared from the polymerization of n-butyl α-hydroxymethyl acrylate at 50 minutes. The scale bar is 1 μm. The particle size determined by DLS is 1.13 μm.
Figure 2D:
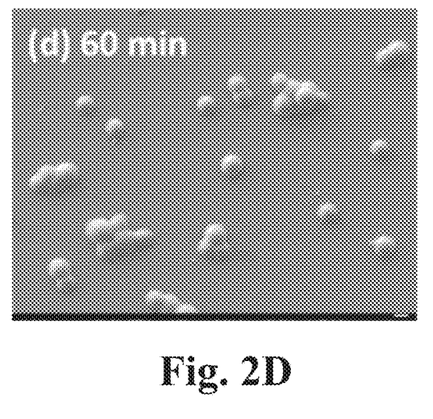
FIG. 2D provides an SEM image showing the formation of latex particles prepared from the polymerization of n-butyl α-hydroxymethyl acrylate at 60 minutes. The scale bar is 1 μm. The particle size determined by DLS is 1.23 μm.
Figure 2E:
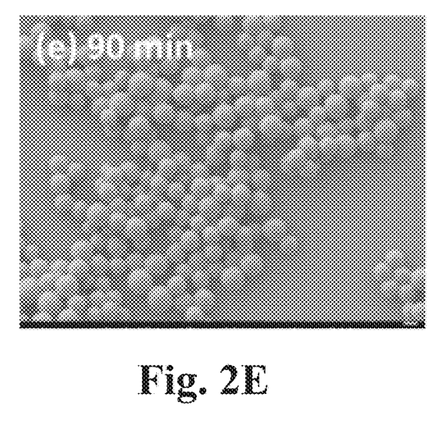
FIG. 2E provides an SEM image showing the formation of latex particles prepared from the polymerization of n-butyl α-hydroxymethyl acrylate at 90 minutes. The scale bar is 1 μm. The particle size determined by DLS is 1.30 μm.
Figure 2F:
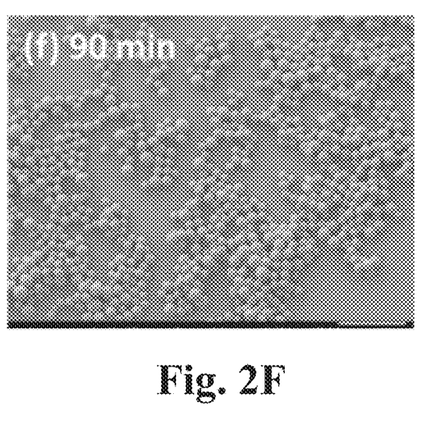
FIG. 2F provides an SEM image showing the formation of latex particles prepared from the polymerization of n-butyl α-hydroxymethyl acrylate at 90 minutes. The scale bar is 10 μm. The particle size determined by DLS is 1.30 μm.

The formation of the latex particles was followed by scanning electron microscopy (SEM) and dynamic light scattering (DLS). FIGS. 2 A-F shows the SEM images of the polymer latex (P2) at different polymerization times (20, 40, 50, 60 and 90 min). 40 minutes after the start of polymerization spherical particles around 1 μm (1.02 μm determined by DLS) were observed [FIG. 2 B]. After that, the particles grew slowly [FIG. 1 (C-F)] and the final latex particle size was 1.30 μm, as determined by DLS.

Since it has been shown that ionic initiators such as potassium persulfate can be used to stabilize the growing particles by their sulfate groups, it was important to verify if the COO— group of the initiator (ABCVA) used in this study was contributing to the self-emulsion polymerization observed. A control experiment in which the surfactant-free emulsion polymerization of n-butyl acrylate using ABCVA was attempted under the same conditions gave an unreacted mixture with monomer droplets coalescing as a separate layer on top of the water. This result indicates that the COO— group derived from the initiator is insufficient to stabilize the growing particles and therefore has a low contribution to the self-emulsion polymerization.

This type of self-emulsion polymerization can also be performed under RAFT polymerization conditions. As an example, we prepared the homopolymer of 2 via emulsion RAFT polymerization. In order to facilitate the transfer of RAFT agent between the oil and water phases, we chose 2-(butylthiocarbonothioylthio)-2-methylpropanoic acid (BMPA) as the RAFT agent. At a reagent ratio $[M]_0/[CTA]_0/[I]_0$ of 220:1:0.2, the polymerization was carried out at 70° C. for 3 hours. The experimental results (Table 2) showed that the molecular weight was well-controlled since the theoretical molecular weight based on the monomer conversion was close to the molecular weight determined by SEC. A good living character was indicated by a PDI of 1.24. Compared to our previous results of solution RAFT polymerization of this monomer (58% conversion in 24 h), the self-emulsion polymerization is much more efficient, which reached 96% conversion in 180 minutes. The size of the latex particle is smaller than that made by conventional radical polymerization via SEP. Also, the latex particles formed under RAFT conditions are more uniform compared to those formed under conventional conditions (see supporting information for SEM images).

It is known that particles tend to aggregate into larger particles to lower their surface energy. In the latex particles formed under RAFT conditions, the additional COO— end groups of the RAFT agent stabilize both the micelles where polymerization occurs and the resulting polymer particles thereby reducing the chance of aggregation. However, under the conventional conditions, the stabilization of the particles due to the COO— of ABCVA, which is present in much lower concentration, is insufficient and the particles would aggregate to lower their surface energy. Therefore, the particles formed under RAFT conditions showed smaller particle size compared to those formed under conventional conditions.

It has been shown that amphiphilic (surface-active) RAFT agents, such as the sodium salt of 2-(dodecylthiocarbonothioylthio)-2-methylpropanoic acid (TTCA), can be utilized to stabilize the growing particles and control the molecular weight. The RAFT agent used in this work also has an amphiphilic structure similar to TTCA, but has a much shorter alkyl chain. Therefore, as a control experiment we carried out surfactant-free emulsion polymerization of n-butyl acrylate with the same amount of ABCVA (initiator) and BMPA (RAFT agent) as that used in the experiments reported in Table 2. However, this control polymerization provided a reaction mixture with an unreacted monomer layer on the top of the aqueous layer, indicating that the BMPA has a low contribution to the self-emulsion polymerization at the concentration used in this work.

TABLE 2

RAFT (co)polymerization of n-butyl a-hydroxymethyl acrylate via SEP

| Polymer[a] | Composition (P2/PBA)[b] | Conversion (%)[b] | $M_n^{theory}$ (kDa)[c] | $M_n^{SEC}$ (kDa)[d] | PDI $(M_w/M_n)$[d] | $T_g$ (°C.)[e] | $D_z$ (nm)[f] |
|---|---|---|---|---|---|---|---|
| P2* | 1.00/0.00 | 96 | 33.8 | 34.0 | 1.24 | 65 | 537 |
| P2(0.75)-r-PBA(0.25) | 0.74/0.26 | ≥99 | 34.2 | 30.0 | 1.23 | 38 | 513 |
| P2(0.50)-r-PBA(0.50) | 0.49/0.51 | ≥99 | 32.8 | 32.4 | 1.08 | −6 | 316 |
| P2(0.25)-r-PBA(0.75) | 0.29/0.71 | ≥99 | 30.8 | 34.0 | 1.10 | −36 | 329 |

P2: poly(n-butyl α-hydroxymethyl acrylate); PBA: poly(n-butyl acrylate);
P2*: poly(n-butyl α-hydroxymethyl acrylate) made by RAFT polymerization
[a]All the experiments were carried out at 70° C. for 180 minutes.
[b]Monomer conversion and the final composition of the polymers were determined by 1H NMR.
[c]Calculated based on the monomer conversion.
[d]Determined by SEC using THF as the eluent.
[e]Glass transition temperature (Tg) was determined by differential scanning calorimetry (DSC).
[f]The average diameter Dz was determined by dynamic light scattering The Baylis-Hillman derived monomer can also be copolymerized with other acrylate monomers by self-emulsion polymerization. As a proof-of-concept, we prepared random copolymers of 2 and n-butyl acrylate in different ratios. As shown in Table 2, the percentage of n-butyl acrylate varied from 25% to 75%. The synthesis of the random copolymers was also efficient and the conversion reached more than 96% in 180 minutes. The polymerization showed good control of the molecular weight and resulted in polymers with low PDI (from 1.08 to 1.23). The structure of the copolymers was confirmed by $^1$H NMR spectroscopy. The final compositions of the copolymers calculated based on the $^1$H NMR integration of the two components were close to the initial feed ratios as determined by comparing the $^1$H NMR integration of the backbone protons of P2 and PBA.

Figure 3:
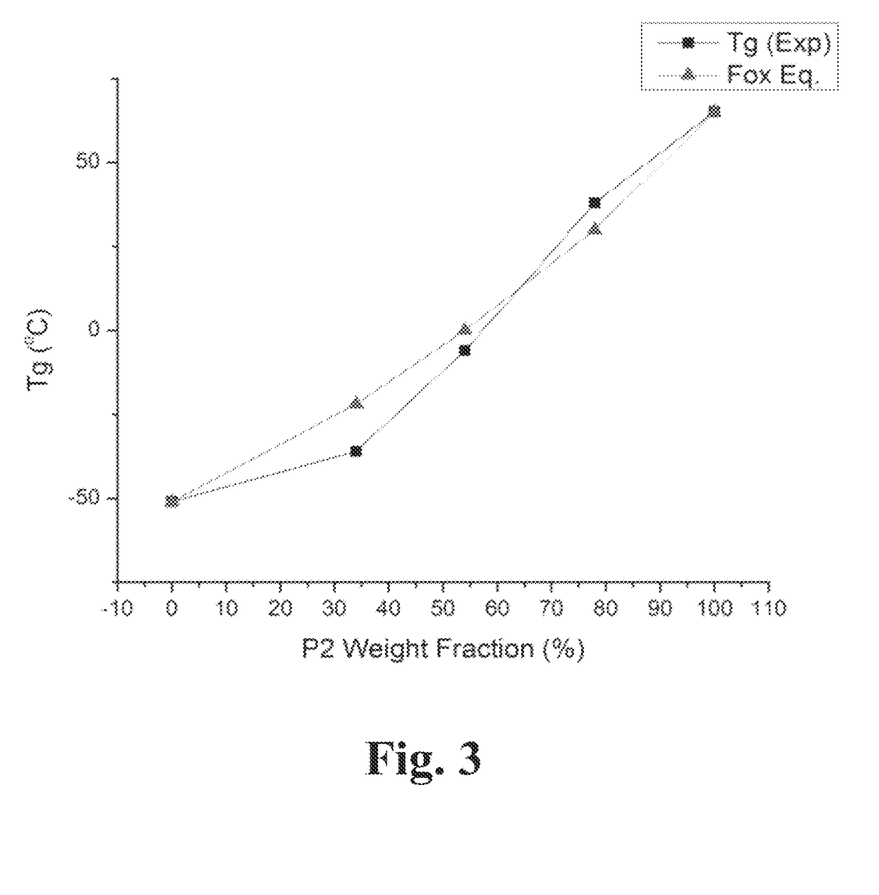
FIG. 3 provides a chart showing the comparison of experimental Tg values (DSC) and those predicted by the Fox equation. (■): Tg determined by DSC. (▲): Tg calculated from Fox equation.

As expected the glass transition temperature of the copolymers varied with the polymer composition. Differential scanning calorimetry (DSC) showed that the $T_g$ of the homopolymer P2* is 65° C., while the $T_g$ of poly(n-butyl acrylate) is −51° C. With increasing fraction of P2, the $T_g$ of the copolymers increase, for example, the $T_g$ of P2(0.25)-r-PBA(0.75) is −36° C. while the $T_g$ of P2(0.50)-r-PBA(0.50) is −6° C. (Table 2). The experimental results of the $T_g$ obtained from DSC was compared to the theoretical results calculated from Fox equation (Eq. 1). $w_1$ and $w_2$ are the weight fractions of component 1 and 2; $T_{g,1}$ and $T_{g,2}$ are the glass transition temperatures of pure component 1 and 2.

$$\frac{1}{T_g} = \frac{w_1}{T_{g1}} + \frac{w_2}{T_{g2}} \qquad (1)$$

It is seen that the experimental results have a good correlation with the values predicted by the Fox equation (FIG. 3).

In addition, our results show that a minor amount (5%) of 2 can be exploited as a polymerizable surfactant for the emulsion polymerization of n-butyl acrylate. The polymerization of n-butyl acrylate was attempted under both conventional radical and RAFT polymerization conditions. It was found that polymerization under conventional radical conditions afforded almost quantitative conversion (≥99%) in 90 minutes providing a polymer with very high molecular weight ($M_n^{SEC}$=786.1 kDa, PDI=1.39). Under RAFT polymerization conditions, the polymerization reached 95% in 180 minutes and showed good control of molecular weight ($M_n^{SEC}$=21.7 kDa, PDI=1.27, $M_n^{theory}$=28.0 kDa). A small high molecular weight shoulder was observed in the SEC trace (see supporting information), which may be due to termination by coupling. The size of the latex particles formed under conventional radical and RAFT polymerization condition was 794 nm and 269 nm, respectively. The merit of monomer 2 is that it would become an integral part of the polymer at the end of the polymerization, which avoids the problem of surfactant migration during the use of the product. Also, when compared to other polymerizable surfactants such as mono-fluoroalkyl maleate or sodium vinylbenzylsulfosuccinate, the structure of 2 is much closer to n-butyl acrylate. Therefore, it is likely that the similarity of the structures would minimize undesirable effects of the surfactant on the latex product.

The current work demonstrates that amphiphilic alkyl α-hydroxymethyl acrylate monomers can be efficiently polymerized via self-emulsion polymerization under conventional radical and RAFT polymerization conditions. Polymerization with almost quantitative conversions can be achieved under both conditions in a short time. By introducing a RAFT agent, the polymerization can generate (co)polymers with controlled molecular weight and low polydispersity. This work also demonstrates that a low percentage (5%) of α-hydroxymethyl acrylate can be used as a polymerizable surfactant for the emulsion polymerization of n-butyl acrylate, which would avoid the side effect of surfactant migration.

What is claimed is:

1. A method of preparing a polymer comprising:
   an emulsion polymerization that employs at least one α-hydroxymethylacrylate as a reactive surfactant and does not employ an additional surfactant other than the at least one α-hydroxymethylacrylate,
   where the at least one α-hydroxymethylacrylate is defined by the formula:

where $R^2$ is a hydrocarbon group with at least 3 carbon atoms.

2. The method of claim 1, wherein the α-hydroxymethylacrylate is defined by the formula where $R^2$ is a hydrocarbon group selected from the group consisting of n-propyl, n-butyl, t-butyl, n-pentyl, n-hexyl, 2-ethylhexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, and benzyl.

3. The method of claim 1, where the polymerization is initiated with water-soluble free radical initiator.

4. The method of claim 1, where the polymerization is mediated with a Reversible Addition-Fragmentation chain Transfer agent.

5. The method of claim 1, where the polymerization further includes a monomer selected from the group consisting of acrylonitrile, alkyl acrylates, alkyl methacrylates, acrylic acid, methacrylic acid, styrene, and combinations thereof.

6. The method of claim 1, where the emulsion polymerization produces a polymer with an α-hydroxymethylacrylate unit that includes a hydroxyl group defined by the following formula where $R^2$ is a hydrocarbon group with at least 3 carbon atoms.

7. The method of claim 6, where the hydroxyl group is reacted with compound selected from esters, carboxylic acid anhydrides, halogen phosphonates, lactones, cyclic carbonates, and lactides.

8. The method of claim 1, where the α-hydroxymethylacrylate has a critical micelle concentration, and the emulsion polymerization takes place in an emulsion polymerization system that includes an amount of the α-hydroxymethylacrylate above the critical micelle concentration of the α-hydroxymethylacrylate.

9. The method of claim 1, where the emulsion polymerization takes place in an emulsion polymerization system that includes a molar percentage based on the total monomer content of the α-hydroxymethylacrylate that is greater 1%.

10. A latex comprising:
a polymer with units derived from the emulsion polymerization of at least one α-hydroxymethylacrylate employed as a reactive surfactant, where no additional surfactant other than the at least one α-hydroxymethylacrylate is employed;
where the at least one α-hydroxymethylacrylate is defined by the formula:

where $R^2$ is a hydrocarbon group with at least 3 carbon atoms.

11. The latex of claim 10, where at least 5% of the polymer units are derived from the polymerization of α-hydroxymethylacrylate.

12. The latex of claim 10, where the polymer further includes units derived from the polymerization of a monomer selected from the group consisting of acrylonitrile, alkyl acrylates, alkyl methacrylates, acrylic acid, methacrylic acid, styrene, and combinations thereof.

13. The latex of claim 10, where the polymer is defined by the formula where each $R^2$ is individually a hydrocarbon group with at least 3 carbon atoms and n is about 100 to about 2000 units.

14. The latex of claim 10, where the polymer is a copolymer defined by the formula where each $R^2$ is individually a hydrocarbon group with at least 3 carbon atoms, each $R^3$ is individually the side chain of a acrylonitrile, alkyl acrylates, alkyl methacrylates, acrylic acid, methacrylic acid, styrene, each $R^4$ is individually a hydrogen atom or a hydrocarbon group, and n is about 100 to about 5000 units, and o is about 100 to about 10000 units.

15. The latex of claim 10, where the polymer is prepared using a RAFT agent and the polymer is defined by the formula where each $R^2$ is individually a hydrocarbon group with at least 3 carbon atoms, n is about 50 to about 1000 units, and Z is a segment of a RAFT agent.

16. The latex of claim 10, where the polymer is a copolymer prepared using a RAFT agent and the polymer is defined by the formula where each $R^2$ is individually a hydrocarbon group with at least 3 carbon atoms, each $R^3$ is individually the side chain of a acrylonitrile, alkyl acrylates, alkyl methacrylates, acrylic acid, methacrylic acid, or styrene monomer, each $R^4$ is individually a hydrogen atom or a hydrocarbon group, n is about 50 to about 1000 units, o is about 50 to about 1000 units, and Z is a segment of a RAFT agent.

* * * * *